United States Patent [19]

Van Derdoes et al.

[11] Patent Number: 5,010,884
[45] Date of Patent: Apr. 30, 1991

[54] EXPANDABLE METAL TRACHEOSTOMY BAND

[76] Inventors: Arthur E. Van Derdoes, 3324 Beech, Port Arthur, Tex. 77642; Jerry A. Van Derdoes, 3737 Locust, Port Arthur, Tex. 77642

[21] Appl. No.: 580,111

[22] Filed: Sep. 10, 1990

[51] Int. Cl.$^5$ .............................................. H61M 16/00
[52] U.S. Cl. ...................... 128/207.17; 128/DIG. 26
[58] Field of Search ................. 128/207.17, DIG. 26, 128/200.26, 911, 912, 207.29, 207.16, 207.15; 604/308; 63/5.1, 5.2

[56] References Cited

U.S. PATENT DOCUMENTS

| | | | |
|---|---|---|---|
| 1,147,467 | 7/1915 | Varga | 63/5.1 |
| 2,039,142 | 4/1936 | Brehm | 128/207.17 |
| 3,994,126 | 11/1976 | Rieth | 63/5.1 |
| 4,313,437 | 2/1982 | Martin | 128/207.17 |
| 4,331,144 | 5/1982 | Wapner | 128/207.17 |

Primary Examiner—Edgar S. Burr
Assistant Examiner—Stephen R. Funk

[57] ABSTRACT

A stainless steel expandable tracheostomy tube holder consisting of a section of stainless steel expandable band (12) and having two tracheostomy attachment hooks (14a) and (14b) affixed on each end, allowing easy attachment to all tracheostomy tubes. Thereby, giving the tracheostomy tube bearer the comfort and durability the stainless steel expandable band affords.

1 Claim, 2 Drawing Sheets

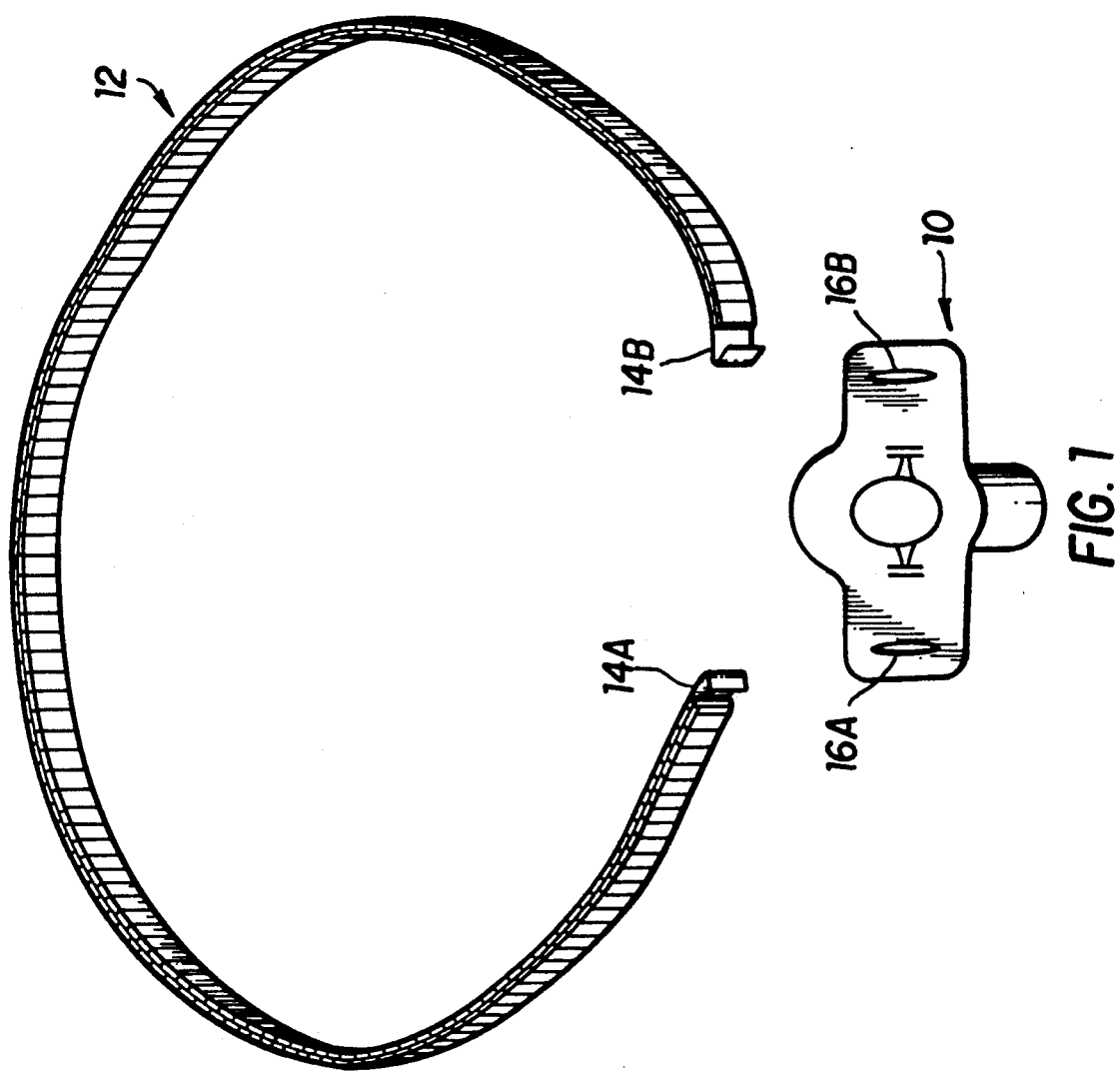

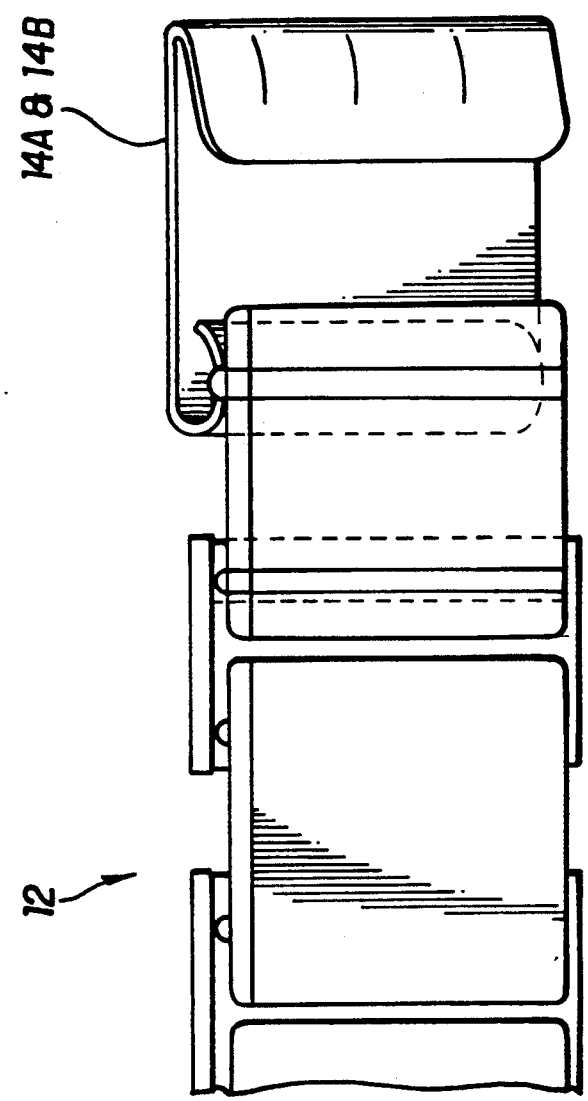

EXPANDABLE METAL TRACHEOSTOMY BAND

BACKGROUND

1. Field of Invention

This invention relates to tracheostomies, specifically an improved tracheostomy holder.

2. Description of Prior Art

All persons being the unfortunate recipient of a tracheostomy due to illness, accidents, etc. have had only two choices of the types of tracheostomy holders available to them.

One being two lengths of surgical type string tied to each end of the tracheostomy tube and then tied around the neck of the wearer.

The other, an adjustable tracheostomy holder patented to Dale Medical Products, Inc. under U.S. Pat. No. 4,331,144.

The string type holder being unsightly and hard to operate by oneself. On the other hand the Dale Tracheostomy Holder provides adjustability, but becomes quickly soiled and are quite hot, thereby generating a lot of perspiration when worn, and at a cost of $4.50 each are quite expensive to say the least.

You can wash the Dale Tracheostomy Holder only to find that the holder has become misshapen and the velcro closure doesn't function properly.

The reason I, Arthur E. VanDerdoes am aware of these shortcomings in the prior art is that I also have a tracheostomy and can sympathize with persons dealing with these problems, which brought me to the conception of the VAN & SON TRACH BAND.

OBJECTS AND ADVANTAGES

During the conception of the VAN & SON TRACH BAND, I concentrated on alleviating several problems found in the prior art, namely, comfort, hygiene, cost, ease of use, durability, and the aesthetic qualities. I firmly believe I have found the solutions to these problems faced by tracheostomy bearers, in the development of the VAN & SON TRACH BAND. Let's look at each problem in the prior art and how the VAN & SON TRACH BAND solves them.

A. COMFORT—The VAN & SON TRACH BAND is made of an expandable stainless steel band, designed to supply a slight amount of tension, thereby not binding during normal movements such as can be encountered while sleeping, bending over, etc. During the period that I wore the Dale Tracheostomy Tube Holder, I noticed that while I slept, the Dale Trasch Holder would bind on the sheets and pillow cases causing the tracheostomy tube to move inside my windpipe, awakening me instantly and finding myself choking and gagging. Since I have worn the VAN & SON TRACH BAND, I have not been awakened like before, thereby I have enjoyed hours of rest that I have previously lost.

B. HYGIENE—Previously made tracheostomy holders, namely, the holder manufactured by Dale Medical Products U.S. Pat. No. 4,331,144 becomes quickly soiled and saturated by dirt, sweat, and numerous other foreign particles, usually in less than twenty-four hours. As previously discussed, washing renders the Dale Trach Holder misshapen and dingy looking.

The VAN & SON TRACH BAND is made from expandable stainless steel. All you have to do is put the VAN & SON TRACH BAND in a cup of hydrogen peroxide or any other suitable cleanser, brush it with an old toothbrush, rinse, wipe dry and you're ready for another three to four days of clean odor free wear.

C. COST EFFECTIVENESS—As discussed previously, the Dale Trach Holder will give you two days maximum bearable wear and at a cost of $4.50 each. That comes to $67.50 per month, or $810.00 per year, an expensive price to pay. The VAN & SON TRACH BAND will cost little more than one month supply of the Dale Trach Holder, and due to the stainless steel construction of the VAN & SON TRACH BAND, it will give years of trouble free service.

D. EASE OF USE—The VAN & SON TRACH BAND can easily be put on or taken off to clean by the wearer without the aid of an outside party. This can be of great importance to a tracheostomy bearer who lives alone. The Dale Trach Holder U.S. Pat. No. 4,331,144 shows in its illustrated instructions a trach bearer having his Dale Tracheostomy Holder being put on by an outside person. Not so on the Van & SON TRACH BAND. The one piece expandable design allows the wearer to just slip the VAN & SON TRACH BAND around the neck, and hook the tracheostomy attachment hooks into the slots provided in the tracheostomy tube face plate. The band's expandable design affords a slight tension, thereby giving a firm attachment to the tracheostomy tube and a secure, comfortable feeling to the tracheostomy bearer.

E. DURABILITY—The VAN & SON TRACH BAND due to its stainless steel construction will offer its wearer years of problem free service. Prior art discussed to my knowledge are all disposal and are only adding to the world's ecological and refuse disposal problems.

F. AESTHETIC QUALITIES—The VAN & SON TRACH BAND is made from polished stainless steel expandable bands. Thereby, giving the appearance of a fine piece of jewelry rather than that of a medical prosthesis.

DRAWING FIGURES

In the drawings, closely related figures have the same number but different alphabetic suffixes.

FIG. 1 shows an overall view of the VAN & SON TRACH BAND and how it relates to and attaches to a tracheostomy tube.

FIG. 2 shows a close up view of the tracheostomy attachment hooks and how they are attached to the trach band.

REFERENCE NUMERALS IN DRAWINGS

10—tracheostomy tube
12—stainless steel expandable band
14a—right side tracheostomy attachment hook
14b—left side tracheostomy attachment hook
16a—right side holder attachment slot
16b—left side holder attachment slot

DESCRIPTION OF FIGS. 1 AND 2

FIG. 1 shows an overall view of my invention, the VAN & SON TRACH BAND. FIG. 1 also shows the stainless steel expandable band 12. The trach band is made by using two or three expandable watch bands and splicing them together to create a solid section of expandable band 12 sufficient length as to fit around the neck of the tracheostomy tube bearer, and by use of the tracheostomy attachment hooks 14a and 14b. Then the tracheostomy band 12 is secured to the tracheostomy tube 10.

FIG. 2 shows a close up view of the tracheostomy attachment hook 14a or 14b and a portion of the trach band 12, and how they are interconnected. Let me explain. On one end of the stainless steel expandable trach band 12, there is an open link with an open unused end. By bending a thin strip of appropriate sized stainless steel, then looping it through the open link and crimping the strip of stainless steel closed, thereby holding it securely to band 12 and the free end having a suitable outward bend so that it easily attaches itself to tracheostomy tube holder slots 16a and 16b in FIG. 1 by a hooking motion. And there you have the tracheostomy attachment hooks 14a and 14b.

OPERATION OF FIGS. 1 AND 2

As discussed in previous paragraphs, the VAN & SON TRACH BAND'S stainless steel expandable band 12 in FIGS. 1 and 2 is used to offer comfort, durability, and flexibility to the bearer of a tracheostomy tube 10.

The tracheostomy attachment hooks labelled 14a and 14b in FIGS. 1 and 2 are designed for ease of use, by inserting them into tracheostomy tube slots 16a and 16b in FIG. 1, thereby joining the stainless steel trach band 12 to the tracheostomy tube 10 and affording the wearer freedom to move about without binding due to the expandability of trach band 12.

SUMMARY, RAMIFICATIONS, SCOPE

Accordingly the reader will see the stainless steel construction will offer durability, flexibility, and comfort. Other advantages are:

a. the ease of use due to the unique design of the tracheostomy attachment hooks;
b. the stainless steel expandable construction allows easy cleaning with an old toothbrush and hydrogen peroxide or other suitable solutions; and
c. the cost efficient use due to a one time cost. All prior art to my knowledge are disposable as in the case of the Dale Trach Holder U.S. Pat. No. 4,331,144.

Although the descriptions above contains many specificities, these should not be thought of as limiting the scope of my invention, but as merely providing illustrations of some of the preferred embodiments of this invention. For example, the tracheostomy attachment hooks could also be changed to snaps, clasp, etc. The stainless steel expandable band for aesthetic purposes could be changed to gold, silver, aluminum, or any other non-corrosive metal.

Thus the scope of my invention should be determined by the appended claims and their legal equivalents, rather than by the examples given.

We claim:

1. In combination a tracheostomy tube and an expandable metal tracheostomy tube holder comprising: a non-corrosive metal expandable band and a tracheostomy tube, said band including resilient means tending to maintain said band in a non-expanded condition, said band having a metal hook affixed on each end and being of sufficient length to fit around the neck when expanded, said hooks attaching said band to said tracheostomy tube whereby said band is expandable to fit around the neck and said resilient means maintains said band and, therefore, said tracheostomy tube in place with a non-binding fit.

* * * * *